United States Patent [19]

Dumican et al.

[11] Patent Number: 4,987,665
[45] Date of Patent: Jan. 29, 1991

[54] PROSTHETIC TUBULAR ARTICLE

[75] Inventors: Barry L. Dumican, Newtown; Barbara Andrews, Bethel, both of Conn.

[73] Assignee: American Cyanamid Company, Stamford, Conn.

[21] Appl. No.: 171,607

[22] Filed: Mar. 22, 1988

Related U.S. Application Data

[63] Continuation-in-part of Ser. No. 146,510, Jan. 21, 1988, which is a continuation of Ser. No. 835,493, Mar. 3, 1986, Pat. No. 4,792,336.

[51] Int. Cl.$^5$ .............................................. D02G 1/02
[52] U.S. Cl. .......................................... 28/218; 28/220
[58] Field of Search ................. 57/247, 284, 287, 289; 28/218, 220, 240, 249, 271

[56] References Cited

U.S. PATENT DOCUMENTS

| | | | |
|---|---|---|---|
| 3,879,928 | 4/1975 | Usdan | 57/157 |
| 4,128,989 | 12/1978 | Bromley et al. | 57/247 |
| 4,693,071 | 9/1987 | Morrison | 57/289 |

OTHER PUBLICATIONS

Man-Made Textile Encyclopedia, Textile Book Publishers, N.Y., 1959; pp. 222, 223 and 238-240.

Primary Examiner—Werner H. Schroeder
Assistant Examiner—Bradley Kurtz DeSandro
Attorney, Agent, or Firm—Charles F. Costello, Jr.

[57] ABSTRACT

The invention involves a method to texturize absorbable or absorbable/nonabsorbable components that are to be used to fabricate textile grafts of all sizes, and specifically for repair of the peripheral vascular system and for coronary bypass use. The bioabsorbable component of the graft fosters increased tissue ingrowth into the graft as compared to conventional 100% nonabsorbable grafts. Increased tissue ingrowth leads to greater patency through formation of a vascularized neointima and less tendency to be aneurysmal through formation of a suitable adventitia. The absorbable component can be a variety of materials, including PGA, the polymer used to manufacture the MAXON ™ suture, etc., whereas the nonabsorbable component (to be used as the backbone) can be new materials, e.g. the polymer used to manufacture the NOVAFIL ® suture, or more conventional polymers, including polyester, polyamide or polypropylene.

12 Claims, 2 Drawing Sheets

PROSTHETIC TUBULAR ARTICLE

CROSS-REFERENCE TO RELATED APPLICATIONS

This application is a continuation-in-part of U.S. Ser. No. 146,510 filed Jan. 21, 1988, which is a continuation of U.S. Ser. No. 6/835,493 filed Mar. 3, 1986, now U.S. Pat. No. 4,792,336 issued Dec. 20, 1988; and also is related to U.S. Ser. No. 6/929,577 filed Dec. 24, 1986, now U.S. Pat. No. 4,871,365 issued Oct. 3, 1989, which is a continuation application of U.S. Ser. No. 727,326 filed Apr. 25, 1985, now U.S. Pat. No. 4,652,264 issued Mar. 24, 1987.

BACKGROUND OF THE INVENTION

This invention relates to a prosthetic article and specifically to a vascular graft containing texturized absorbable or absorbable/nonabsorbable biomaterial. The use of the vascular graft is for repair of the peripheral vascular system and for coronary bypass.

The absorbable material fosters increased tissue ingrowth into the graft as compared to nonabsorbable grafts. Increased tissue ingrowth leads to greater patency through formation of a vascularized neointima and less tendency to be aneurysmal through formation of a suitable adventitia.

The absorbable material can vary and includes polyglycolic acid (hereafter PGA), and a copolymer comprising glycolic acid ester and trimethylene carbonate linkages, e.g. the copolymer in the MAXON TM (American Cyanamid Company, Wayne, N.J. 07470 U.S.A.) suture.

The nonabsorbable material (which is used as the backbone) can be proprietary materials, e.g. a Hytrel TM (E. I. DuPont and Co., Wilmington, Del. U.S.A.) polymer, such as the polymer in the NOVAFIL TM (American Cyanamid Company, Wayne, N.J.) suture. Alternatively, the nonabsorbable material can be more conventional polymers including a polyester, polyamide or polypropylene.

There has been a long felt need in the vascular graft art to develop a small diameter graft which will be generally acceptable to essentially all of the surgical community. The reasons for this long felt need are many and relate both to the biological requirements for a small diameter graft and to the limitations of the biomaterials generally used for these applications. Consequently, prior art small diameter vascular grafts, e.g. at 50 or less than 8 mm diameter to even smaller diameter grafts, e.g. at or less than 4 mm diameter, have not been universally accepted by the surgical community.

Further discussion of the development of this long felt need is disclosed in U.S. Pat. No. 4,652,264 issued Mar. 24, 1987 at column 1 line 43 to column 2 line 12, which patent is incorporated herein by reference.

For a discussion of the background of this invention in a connective tissue repair or augmentation device, see U.S. Ser. No. 06/835,493 filed Mar. 3, 1986 page 1 to page 7 line 3 which is incorporated herein by reference.

SUMMARY OF THE INVENTION

A tubular article useful in prosthetic surgery has been invented. The article has a plurality of texturized fibers manufactured from an absorbable polymer. The polymer comprises at least one trimethylene carbonate linkage. In one embodiment, the absorbable polymer is a copolymer. In another embodiment, the article is manufactured on a warp knitting machine. The absorbable polymer comprises more than about 50% by weight of the article. The remainder of the article, if any, comprises a plurality of texturized fibers manufactured from a nonabsorbable polymer.

Another embodiment is an article manufactured on a weft knitting machine. The absorbable polymer comprises more than about 50% by weight of the article. The remainder of the article, if any, comprises a plurality of fibers manufactured from a nonabsorbable polymer.

Yet another embodiment is a woven article. The absorbable polymer in the texturized warp and weft yarns comprises more than about 50% by weight of the article. The remainder, if any, comprises a plurality of texturized fibers manufactured from a nonabsorbable polymer.

A generic embodiment of all of the above is a tubular article comprising a vascular graft.

A vascular graft has also been invented. The vascular graft has a plurality of texturized fibers which are manufactured from an absorbable copolymer. The copolymer comprises up to about 50% by weight of trimethylene carbonate linkages. The copolymer in the MAXON TM (American Cyanamid Company, N.J. U.S.A.) suture contains a copolymer having trimethylene carbonate linkages. MAXON TM, which is a poly(glycolide-co-trimethylene carbonate), has superior and unexpected properties when contrasted to other absorbable fibers. It is long-lasting. A portion of its original strength is retained out to 56 days; 50% of the strength remains through 28 days. The absorption rate of MAXON TM is approximately equal to PGA.

A MAXON TM fiber is more compliant than polyglycolic acid (herein PGA). A graft containing 75% MAXON TM in combination with Dacron TM has a measured compliance of 3.03. A similarly constructed PGA/Dacron TM graft has a compliance of 2.45. Compliance is measured as a percentage of diametral change per 100 mm Hg internal pressure change. Finally, the bending modulus of MAXON TM is approximately 325,000 p.s.i., indicating that MAXON TM is a much more flexible fiber than other absorbable fibers.

In one embodiment, the copolymer comprises about 50% by weight of glycolic acid ester linkages. In another embodiment, the copolymer consists of at least one glycolic or lactic acid ester linkage.

Another embodiment is a graft which is manufactured on a warp knitting machine. The absorbable polymer comprises more than about 50% by weight of the article. The remainder, if any, comprises a plurality of texturized fibers manufactured from a nonabsorbable polymer. In a specific embodiment, the graft is manufactured on a Raschel knitting machine. In another specific embodiment, the plurality of texturized nonabsorbable polymer fibers of the graft comprises about 20 to 35% by weight of the graft.

The plurality of absorbable and nonabsorbable fibers are separately texturized by either a false twist or a knit/deknit process. In a most specific embodiment, the nonabsorbable polymer is Hytrel ®. Another most specific embodiment is wherein the nonabsorbable polymer is polyethylene terephthalate.

Hytrel TM is a trademark of E. I. DuPont de Nemours & Co., Wilmington, Del. U.S.A. for a class of polymers having the following generic formula:

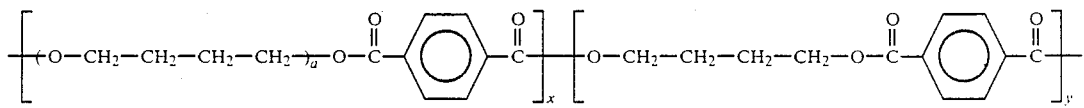

polytetramethylene glycol terephthalate     polybutylene terephthalate

The values for a, x and y are known from the prior art, e.g. as disclosed in "Thermoplastic Copolyester Elastomers: New Polymers For Specific End-Use Applications", M. Brown, Rubber Industry 9 102-106 (1978), and the references (footnote numbers 1b 1c 1d 2 and 3) cited therein; Encyclopedia of Polymer Science and Technology, Supplement, 2 485-510, see particularly pages 486 to 493, Interscience N.Y. 1977; and U.S. Pat. No. 4,314,561 issued Feb.9, 1982. All of this prior art is incorporated herein by reference. A specific embodiment of Hytrel® which is useful in this invention is a grade of Hytrel® having a 72 durometer D hard.

The polymer in the Novafil TM (American Cyananid Company, N.J., U.S.A.) suture contains Hytrel®. Novafil TM, which is a polybutester, has superior and unexpected properties when contrasted to other nonabsorbable fibers. It is more flexible than other convention-al-type graft fibers, e.g. Dacron TM. Novafil TM has a bending modulus of approximately 230,000 p.s.i. Also, the compliance of a Novafil TM containing graft measures 4.20 in combination with MAXON TM. A similar graft manufactured from Dacron TM and Maxon TM has a compliance of 3.03. Compliance is measured as a percentage of diametral change per 100 mm Hg internal pressure change.

Finally, a tubular article useful in prosthetic surgery and having a plurality of texturized fibers manufactured from a nonabsorbable polymer has been invented. In a specific embodiment, the nonabsorbable polymer is Hytrel®.

A concentric knit relationship, wherein PGA comprises the inner tube, Maxon TM comprises the middle tube, and either Dacron TM Novafil TM comprises the outer tube, has the following synergistic advantages:

(1) Dacron TM is known from the prior art to incite a thrombogenic reaction.
(2) Dacron TM or Novafil TM fibers can be shielded from blood by inner layers of PGA and MAXON TM, thereby minimizing the tendency to thrombose and occlude the graft.
(3) As PGA and then MAXON TM degrade and are absorbed, the inner capsule becomes larger and, hence, has a higher probability of remaining patent in small diameter applications.
(4) Based upon animal studies, a PGA- and MAXON TM- containing graft tends to have greater patency than a commercial graft material.

The concentric relationship can be a plurality of single tubes attached together by sewing, gluing, or merely held together by frictional contact between the layers.

The texturized MAXON TM and/or PGA absorbable components of the graft become absorbed and are replaced by natural tissue. This leaves a skeletal structure of texturized nonabsorbable Dacron TM Novafil TM fibers which is encapsulated in healthy collagenous tissue. The inside wall or neointima of the skeletal structure develops into an endothelial-like growth. The outside wall has been shown to be comprised of a matrix of mature, highly vascularized granulation tissue.

This invention also relates to a nonabsorbable vascular graft manufactured from a Hytrel TM polymer, such as the polymer in the Novafil TM suture.

A method has been invented for texturizing a hydrolytically degradable, bioabsorbable fiber or yarn, or combination of biodegradable and nonabsorbable yarn without significantly degrading the bioabsorbable polymer structure. The purpose of the texturization is to form a plurality of fibers or yarn for use in a vascular graft or other surgical implant that will (1) encourage tissue ingrowth and (2) improve conformability and compliance.

This invention relates to the method of texturizing the absorbable or absorbable/nonabsorbable plurality of fibers or yarn. The method comprises:

(1) twisting, knitting, crimping or otherwise mechanically deforming the plurality of bioabsorbable or combination of absorbable and nonabsorbable thermoplastic fibers or yarn; and
(2) setting the plurality of fibers or yarn from step (1) by
  (a) heating them to their glass transition or softening temperature in a dry atmosphere under a vacuum of up to about 5 torr at a temperature of from about 100° to 190° C., preferably at or less than about 1 torr and a temperature of about 120° to 140° C.; and
  (b) cooling the fibers or yarn to ambient temperature.

Following cooling, the twist or other mechanical deformation is removed from the yarn by the same means in which it was inserted. Because of the heat setting step, the deformation imparted to the yarn is permanently set causing a textured, open, bulky appearance. The mechanical deformation can be removed by reversing the direction of an upstroke twisting (or uptwisting) machine. Such a machine is known in the prior art, e.g. see Man-Made Textile Encyclopedia, Textile Book Publishers, N.Y., 1959 pages 222, 223 and 238 to 240. This prior art is incorporated herein by reference.

This texture can further be modified to a lower degree, in the case of twisted heat set fibers, by subsequently rewinding the yarn onto another package (spool, aluminum tube, paper tube, etc.) under a lower winding tension, reheating the yarn and subsequently cooling it.

For a description of the relative humidity to be used in texturizing a plurality of fibers or yarn manufactured from a glycolic acid homopolymer or copolymer, see U.S. Pat. No. 3,422,181 entitled "Method for Heat Setting ..." which issued to L. Chirgwin on Jan. 14, 1969, which patent is incorporated herein by reference. For a description of general process conditions useful in manufacturing a glycolic acid homopolymeric or copolymeric suture, see U.S. Pat. Nos. 3,626,948 entitled "... Enhanced In-Vivo Strength Retention" which issued Dec. 14, 1971 and 3,772,420 entitled "Method for Improving the In-Vivo Strength ..." which issued Nov.

13, 1973, both to A. Glick, and both incorporated herein by reference.

A drawing which describes the shape and/or geometrical configuration of the texturized plurality of fibers or yarns is not necessary for an understanding of this invention. That is, any person skilled in the texturization art will know how to manufacture and how to use the invention by reading this specification, generally and the examples, specifically.

It is to be understood that the term carrier yarns as disclosed in this specification is synonymous with the term sleeve yarns.

For a description of manufacturing the Hytrel TM polymer, see e.g., U.S. Pat. Nos. 3,766,146; 3,763,109; 3,023,192; and Great Britain Patent No. 1,458,341; for a description of manufacturing the Novafil TM suture, see, e.g., U.S. Pat Nos. 4,224,946 and 4,314,561. All of these patents are incorporated herein by reference.

The materials can be constructed into vascular grafts in several ways: (1) as woven single tubes, (2) as warp or weft knit single tubes, (3) as double triple, etc. concentric tubes, and (4) as single woven or knit tubes that are externally supported. The materials can also be constructed from a fabric having a changing composition, e.g. a graded transition section in a fabric or a bicomponent filament. See U.S. Pat. No. 3,463,158 issued Aug. 26, 1969 entitled Polyglycolic Acid Prosthetic Devices, which is incorporated herein by reference. The graft structures can be either straight or bifurcated (branched) tubes.

A knitted tube can be manufactured on a Raschel knitting machine. The number of needles per inch can be about 25 to 35. The gauge (which is twice the number of needles per inch) can therefore be about 50 to 70. Prior art Raschel knitting machines are commercially available in a 56, 60 or 64 gauge.

A surgical repair device having a length to width ratio of greater than one has been invented. The device comprises a plurality of fibers. The majority of the fibers are in a direction essentially parallel to the device length.

The device has an absorbable component comprising from about 10 to 100 percent of polymer having a glycolic or lactic acid ester linkage. The remainder of the device, if any, has a nonabsorbable component.

In one embodiment of the device, the absorbable polymer is a copolymer having a glycolic acid ester linkage. In a specific embodiment, the copolymer comprises glycolic acid ester and trimethylene carbonate linkages.

A connective tissue repair device having a length to width ratio of greater than one has also been invented. The device comprises a plurality of fibers. The majority of the fibers are in a direction essentially parallel to the device length. The device has an absorbable component comprising from about 10 to 100 percent of a copolymer. The copolymer has glycolic acid ester and up to about 50 percent by weight of trimethylene carbonate linkages. The remainder of the device, if any has a nonabsorbable component. Embodiments of the repair device include a knitted, woven, braided and flat braided device. In one embodiment, the longitudinally oriented majority of the fibers comprises about 80 to 95 percent. In a specific embodiment, the longitudinally oriented majority of the fibers comprises about 90 percent.

In another embodiment, the device has an absorbable component comprising at least about 80 percent. In a specific embodiment, the device has a nonabsorbable component selected from the group consisting of a poly($C_2$–$C_{10}$ alkylene terephthalate), poly($C_2$–$C_6$ alkylene), polyamide, polyurethane and polyether-ester block copolymer. In a more specific embodiment, the device consists of poly(ethylene terephthalate) or poly(butylene terephthalate) as the poly($C_2$–$C_{10}$ alkylene terephthalate), and a polybutester as the polyether-ester block copolymer. In a most specific embodiment, the device consists of Hytrel TM as the polybutester.

A polybutester can be defined as a polytetramethylene glycol. polymer with terephthalic acid and 1, 4-butanediol. See. e.g.. the definition of polybutester in USAN and the USP dictionary of drug names, U.S. Pharmacopeial Convention, Inc., Md. 20852 U.S.A., 1985.

A flat braided ligament or tendon implant device having a length to width ratio of greater than one has been invented. The device comprises a plurality of fibers. The majority of the fibers are in a direction essentially parallel to the implant length. The braid has about 5 to 100 carrier and up to about 50 warp yarns.

The implant has an absorbable component comprising from about 10 to 100 percent of a copolymer. The copolymer has glycolic acid ester and from about 20 to 40 percent by weight of trimethylene carbonate linkages. The remainder of the implant, if any, has a nonabsorbable component.

In one embodiment of the implant, the braid has about 13 carrier and about 6 warp yarns. In a specific embodiment, the implant consists of about 100 percent of the absorbable component. In a more specific embodiment, the carrier yarns consist of about 100 percent of the absorbable component and the warp yarns comprise about 80 percent of the absorbable component. In a most specific embodiment, the nonabsorbable component in the warp yarns is selected from the group consistent of a poly(ethylene terephthalate) and polyether-ester block copolymer.

In other embodiments of the implant, the yarns are texturized or heat treated. In a further embodiment of the implant. the braid is heat treated.

The bioabsorbable filaments may be comprised of man-made polymers including glycolide-trimethylene carbonate (GTMC), polyglycolic acid, polydioxanone, poly(L-Lactic) acid, poly(DL-Lactic) acid and copolymers or physical combinations of the components of these polymers. Natural bioabsorbable polymers such as regenerated collagen or surgical but may also be used. The biocompatible (nonabsorbable) components include poly(ethylene terephthalate) (PET). poly(butylene terephthalate) (PBT), polyether-ester multi-block copolymers, polypropylene, high strength/modulus polyethylene, polyamide (including polyaramid). or polyether type polyurethanes. Once spun into filaments, the properties of the above materials may be improved for this application by various temperature/time/stress treatments.

The device shall be braided, woven or knitted so that the structure has the desired strength and stiffness in the primary (axial) loading direction. It also has adequate interfibrillar space and minimized thickness to promote the ingrowth of tissue. The end(s) of the device may be compressed inside biocompatible metal sleeve(s) to which swivel end-caps(s) and surgical needle(s) are attached in such a way as to permit rotation of the needle(s) about the longitudinal axis of the device.

In use, an appropriate number of plies of the device are implanted to match the biomechanical properties of the tissue being repaired. This permits an early return to normal function post-operatively. As the ligament or tendon begins to heal, the implant continues to bear any applied loads and tissue ingrowth commences. The mechanical properties of the bioabsorbable component(s) of the implant then slowly decay to permit a gradual transfer of loads to the ingrown fibrous tissue, stimulating it to orient along the loading direction. Additional ingrowth continues into the space provided by the absorbed components of the implant. This process continues until the bioabsorbable component(s) are completely absorbed and only the newly formed tissue remains, or the bicompatible (nonabsorbable) component(s) are left in situ to provide long-term augmentation of the newly formed tissue.

DESCRIPTION OF THE PREFERRED EMBODIMENT

Figure 1:
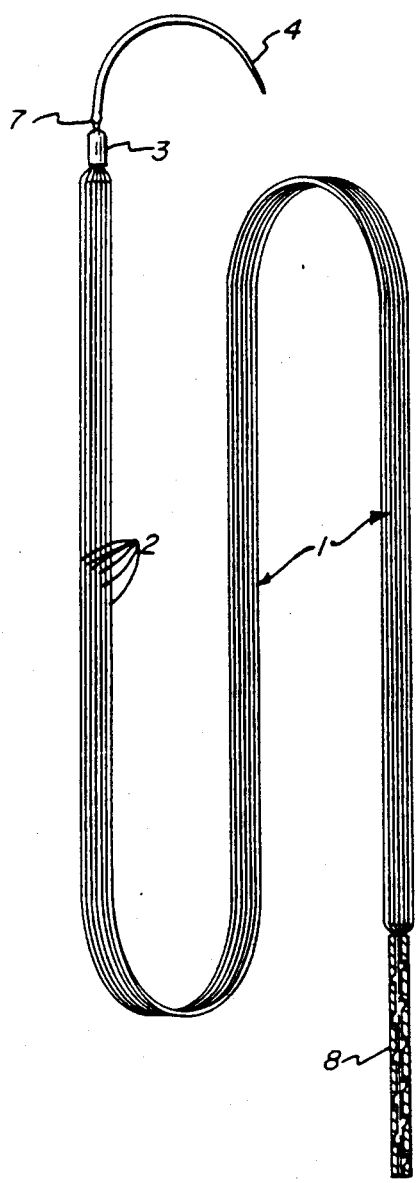
FIG. 1 is a diagrammatic view of the device described as the preferred embodiment, except that two different possible ends are shown.
Figure 2:
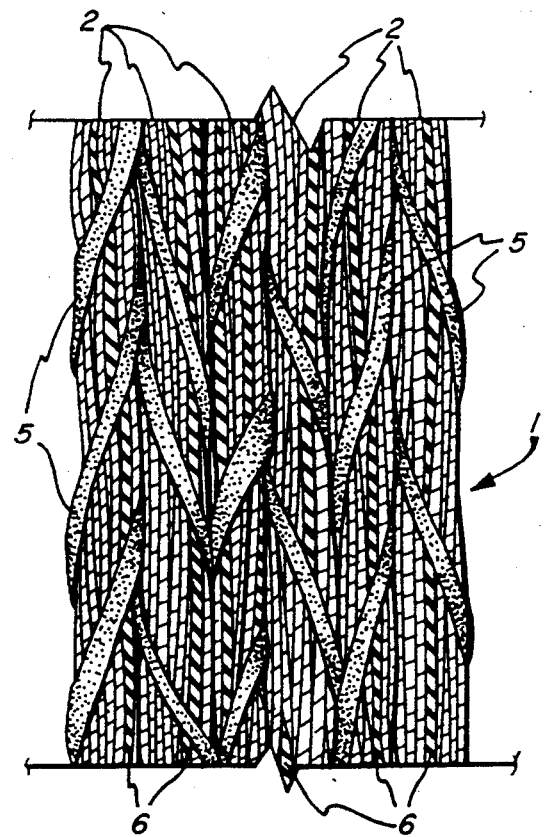
FIG. 2 is an enlarged view of the flat surface of the preferred embodiment showing the braided construction in greater detail.

I.

The following steps are followed when preparing knit vascular grafts starting from the appropriate yarns. The proper denier texturized yarns for the specific construction have to be knit. If the denier to be used can only be obtained by using three or mote ends. the texturized yarn must be ply-twisted together. For example, if the construction is a 330-denier PGA and 100-denier textured Dacron TM, and the only available PGA is 110-denier, it is necessary to twist three ends of 110-denier PGA and the one end of 100-denier Dacron TM. Other variations can be used, depending on the type of construction called for. After ply-twisting onto a king spool, the twisted yarn is transferred to a model 50 cone, using a coning machine. It is preferred that any material that is not twisted and is to be used for knitting be transferred to a cone, or to a similar type package from which the texturized yarn may easily be removed. The method of texturization is described above under "SUMMARY OF THE INVENTION". The texturized yarn is then set up on the knitting machine.

The knitting machine can be commercially available. It can be a floor-type self-contained unit, completely assembled, with exception of the yarn tension or stop-motion assembly. A direct V-belt drive from a fractional horsepower motor to the knitting head allows for a quiet knitting speed up to about 1100 r.p.m. A variable speed take-down assures minimum breakdowns and absolute quality stitch control. Operating speeds can vary depending on cylinder size and also the type of yarn or fibers used.

The proper density of the graft construction is obtained by changing the stitch cam and take-down setrinqs. The stitch cam controls the length of the stitch, and the take-down controls the tension of the tubular fabric being knit.

After knitting, the graft material is scoured in xylene under ultrasonic agitation for two ten-minute baths. The material is allowed to dry in a fume hood until no xylene odors can be detected. The graft material is then cut to appropriate lengths (e.g. 4 mm×60 mm; and/or 8 mm×80 mm) and then reversed.

Reversing involves turning the graft inside out to have a smooth inner surface, and a rougher outer surface to promote ingrowth. Any graft containing PGA is then post-treated on stainless steel mandrels at temperatures of about 115° C. to 150° C., under a vacuum approximately equal to 1 torr or lower. The post-treatment process seems to increase the tensile strength retention for the absorbable component, up to about 60 days after implant. A graft that does not contain PGA may not undergo the post-treatment process.

The ends of the graft may then be heat-sealed on a hot surface to prevent unravelling. During heat-sealing, the ends of the graft are melted only slightly.

Following scouring in xylene or another medically approved nonaqueous solvent and drying, the graft is then packaged in a polycarbonate folding container, which is then placed in a foil inner pouch. The graft is then sent through an absorbable device EtO-sterilization cycle. After sterilization, the graft is repacked in a 2-web TYVEK ® (a spun bonded polyolefin manufactured by E. I. DuPont Co., Wilmington, Del., U.S.A.)-/Mylar TM (a polyethylene terephthalate also manufactured by E. I. DuPont & Co.) pouch, sealed and EtO-sterilized a second time.

A series of in vivo studies with woven vascular grafts in several configurations was completed. The following materials although not exclusive, were included:
(a) PGA/Dacron TM 80/20 low and high porosity. 4 and 6 mm in diameter
(b) PGA/copolymer having glycolic acid ester. and trimethylene carbonate linkages. 4 mm
(c) Woven non-crimped Dacron TM 4 and 6 mm; and
(d) Gore-Tex (a Trademark of Wil-Gore & Associates. Inc.) 4, 8 and 10 mm.

The overall patency rate for PGA containing grafts was substantially higher than controls: 58% vs. 41%.

Bi- and tri-component vascular grafts made of biodegradable and non-degradable fibers have been studied in the beagle. Observations carried out from ~30 days to ~7 months showed that as the absorbable component left the textured graft structure, organized and oriented tissue invaded the graft approximating the location of the degraded material. The tissue ingrowth appeared to mobilize as a neointima with the luminal surface covered by cells strongly resembling endothelium. The non-degradable texturized component exhibited dispersed fibers within a matrix of mature, highly vascularized granulation tissue. This rich blood supply persisted for the period of maximum observation.

The graft structures were provided in two diameters: 4 and 8 mm ID. The former were studied as interpositional grafts in both carotids of the host; the latter as interpositional grafts in the thotacic aorta. The 4 mm grafts (40–60 mm in length) were examined at 1 and 2 months and showed high degrees of patency. The tissue reaction showed progressively increasing tissue incorporation although endothelization was absent at 1 month and only partially manifest at 2 months. The 8 mm grafts examined at ~3-~7 months were uniformly patent and showed uninterrupted complete endothelization of the graft lumen and complete replacement of the degradable material by the tissue elements noted above.

The present invention is illustrated by the following examples which can be useful in peripheral vascular surgery, as coronary artery bypasses or in general arterial or venous grafting.

EXAMPLE 1

This graft is a double-walled structure consisting of a 100% PGA woven inner tube and a 100% texturized knit Dacron TM velour outer tube. The structure was designed so that the inner wall, being PGA, would become absorbed and be replaced by a smooth, well-organized tissue at least partially consisting of endothelial cells. This inner wall would become the new intima. The outer wall, being constructed of porous nonabsorbable Dacron TM material would allow tissue and capillary ingrowth and at the same time, add support to the newly-grown neointima to prevent aneurysms. The Dacron TM outer wall material is a Sauvage Filamentous Veloure fabric supplied by U.S.C.I., a division of C. R. Bard Co., Inc., Billerica, Mass. U.S.A. The inner wall fabric is a woven tube having a 1×1 plain weave construction using 5-ply. 46-denier. 21 filament (PGA) polyglycolic acid yarn in both the warp and filling direction.

The graft materials were scoured in xylene in an ultrasonic bath—2 baths of fresh xylene for 10 minutes each—to remove fiber spin finish.

The outer and inner tubes for the 4 mm I.D. grafts were cut to approximately 45 mm in length. The tubular woven PGA material was mounted on stainless steel rods, placed in a vacuum chamber and treated at 130° C. for 3 hours under a vacuum of less than 1 torr (a similar treatment was done for the 8 mm tubes, except they were cut to 80 mm length).

Next, the inner and outer tubes were stitched together by placing either 3 (4 mm I.D.) or 4 (8 mm I.D.) longitudinal rows of stitches between inner and outer wall. The double tube shafts were then packaged and EtO-sterilized prior to use as implants.

Following graft construction and sterilization, the 4 mm grafts were implanted in the left and right carotid arteries of thoroughbred beagle dogs. The 8 mm I.D. grafts were implanted in the thoracic aorta. The grafts were left in the animal for periods of up to 90 days, at which time the dogs were sacrificed, and the grafts were dissected and removed for subjective and histological examination.

Examination of the implant sites revealed absorption of the PGA fiber and replacement with a smooth, glistening endothelial-like neointima. The Dacron TM outer wall was ingrown with tissue and small blood vessels. There was little, if any, indication of aneurysmal dilation. Exclusive of technical error during implant, grafts Were patent and blood flow, as determined by Doppler recordings. Was satisfactory.

EXAMPLE 2

A 3-ply yarn, consisting of 110-denier/50-filament PGA, 105-denier/25-filament MAXON TM (a copolymer having glycolic acid ester and trimethylene carbonate linkages. e.g as described in U.S. Pat. No. 4,429,080 issued Jan. 31, 1984 and incorporated herein by reference), and 100-denier texturized Dacron TM, was plied together at approximately 2 turns per inch of twist and knit into (a) 4 mm and (b) 8 mm inside diameter (I.D.) tubes. The knitting machine used was a Lamb ST3A circular weft knitting machine. The needle cylinder used had 25 needles per inch of circumference.

Following knitting the tubular graft material was scoured, cut, post-treated, packaged and sterilized as described in Example 1.

The tricomponent structure, being comprised of both MAXON TM (glycolide-TMC) and polyglycolic acid yarns after post-treatment attains a tighter, more pebbly velour-like appearance, due to the differential shrinkage between the two absorbable fibers in the presence of textured Dacron TM.

The 4 mm and 8 mm grafts were implanted in beagle dogs, as described under Example 1.

Examination of the implant sites following sacrifice revealed partial to complete absorption of the bioabsorbable yarns, excellent patency, no noticeable aneurysmal formation and a uniform granular tissue forming the neointima and extending through the wall to the advential surface.

Table 1 is a summary of the in vivo animal data for the knit grafts constructed according to Example 2.

TABLE 1

| SUMMARY OF ANIMAL DATA ON KNIT GRAFTS | | | | | | |
|---|---|---|---|---|---|---|
| Graft Composition | Number Implanted | Implant Site | Number Patent | Aneurysmal Tendency 0123[a] | Number Occluded | Number Unsacrificed |
| 33/33/33 PGA/ | 6 | Thoracic Aorta | 5 | 0041 | — | 1 |
| MAXON TM /Textured | 4 | Left Carotid Artery | 3 | 2010 | 1 | — |
| DACRON ® | 6 | Right Carotid Artery | 3 | 0031 | 2 | 1 |

[a]Rating:
0 = None
1 = Possible
2 = Slight
3 = Significant

EXAMPLE 3

A 4-Ply yarn consisting of three ends of 105-denier DAXON TM (as described in the Background and in Example 2 above) and one end of 100-denier texturized Dacron TM was plied together at a twist level of approximately 2 turns/inch. The yarn was knit into 4 and 8 mm I.D. tubes on separate Lamb ST3A circular weft knitting machines, using 25-needle per inch knitting cylinders. These grafts had wall thicknesses of between 650 and 850 microns.

Following knitting the graft material was scoured, cut out 45 to 80 mm lengths, heat-set at 110° C. for 1 to 3 minutes on stainless steel sizing rods. helically wrapped with 2-0 monofilament MAXON TM suture material as a means of external support packaged and sterilized.

The external support material was attached to the outside surface of the vascular graft, using polymeric glycolide/trimethylene carbonate (TMC) dissolved in methylene chloride as an adhesive. Alternatively, poly-TMC dissolved in methylene chloride can be used as an adhesive. Table 2 is a summary of the in vivo animal data for the knit grafts constructed according to Example 3.

TABLE 2
SUMMARY OF ANIMAL DATA ON KNIT GRAFTS

| Graft Composition | Number Implanted | Implant Site | Number Patent | Aneurysmal Tendency 0123[a] | Number Occluded | Number Unsacrificed |
|---|---|---|---|---|---|---|
| 75/25 MAXON TM / | 6 | Thoracic Aorta | 6 | 2022 | — | — |
| Textured DACRON ® | 3 | Left Carotid Artery | 2 | 1010 | 1 | — |
| with External Support* | 4 | Right Carotid Artery | 4 | 0112 | — | — |

[a]Rating:
0 = None
1 = Possible
2 = Slight
3 = Significant
*External support of monofilament MAXON TM absorbable suture material.

EXAMPLE 4

A 4-ply yarn consisting of two ends of 46-denier PGA, one end of 62-denier PGA and one end of 100-denier texturized NOVAFIL® was assembled at approximately 2 turns per inch of twist. The texturized NOVAFIL® yarn was false-twist texturized, using the Helanca® (trademark of Heberlein Corp., Wattwil, Switzerland) Process in order to provide a surface texture that would encourage maximum tissue ingrowth. The combined yarn was knit into 4 and 8 mm I.D. tubes similar to Example 3, except that the cylinder had a needle spacing of 33 needles per inch.

Following knitting, the graft materials were scoured, cut to 45 and 80 mm length tubes, post-treated on stainless steel rods under vacuum of 1 torr at 130° C. for 3 hours, cooled, helically wrapped with 3-0 MAXON TM monofilament suture material attached to the surface of the graft using poly-TMC as an adhesive and, finally, packaged and sterilized.

EXAMPLE 5

In this warp knit example, 70-denier texturized Dacron TM was combined with 105-denier MAXON TM multifilament yarn on a 48-gauge Raschel knitting machine in the following construction:

| Front Bar | 2/0 | 2/4 | 70-denier textured Dacron TM |
| Back Bar | 2/0 | 4/6 | 105-denier MAXON TM |

EXAMPLE 6

This construction is similar to Example 5, except that the stitch construction is reversed as follows:

| Front Bar | 2/0 | 4/6 | 105-denier MAXON TM |
| Back Bar | 2/0 | 2/4 | 70-denier textured Dacron TM |

Examples 5 and 6, although formed on a 48-gauge Raschel machine can be made on a 56-, 60- or 64-gauge Raschel machine, having 14 or more guide bars, positive feeds and stitch combs.

In preferred embodiments the elongated textile structure 1 of the implant comprises a flat braid having primarily axial (quoit) yarns of an absorbable polymer such as GTMC. The number and denier of quoit and sleeve yarns are varied to provide devices having a range of properties that are biomechanically compatible with any likely implant site. Swivel end cap(s) 3 and surgical needle(s) 4 may be attached at the end(s) of the device to facilitate placement and attachment.

Figure 3:
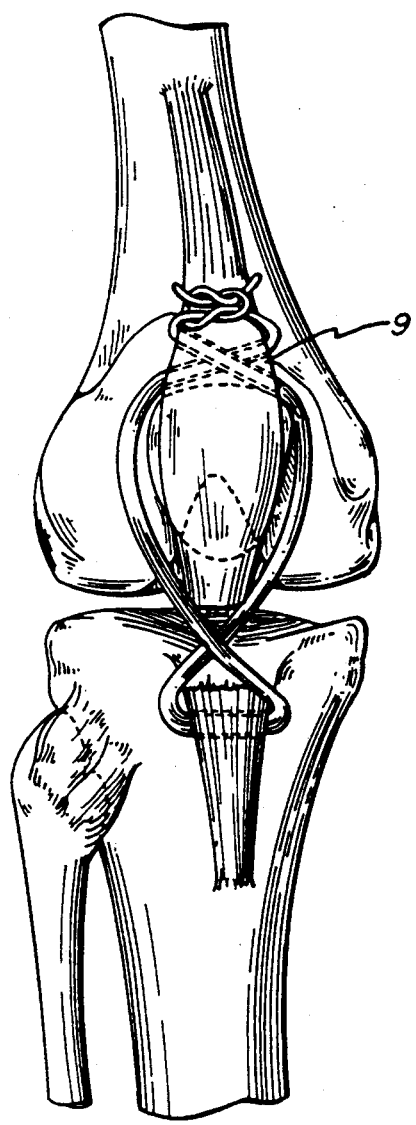
FIG. 3 is an anterior view of a knee showing the device as positioned for repair of the excised patellar ligament in animal (canine) studies.

The procedures described below are followed when preparing flat braids to be used as artificial ligaments/tendons starting from the appropriate yarns. To begin, the proper denier yarns for the specific braid construction are required. This example describes a typical construction designed to fit a particular animal model—repair/replacement of the canine patellar ligament (FIG. 3). An application that had a tensile strength/stiffness requirement three times higher than that described in the example would require three times as much yarn. This could be accomplished by simply tripling the final total braid denier, either by increasing the yarn denier or increasing the number of sleeve and quoit (stuffer yarns) or both.

To produce a braid for canine patellar ligament repair (FIG. 3), a final braid denier between 13,000 and 24,000 is tarqeted. In the preferred construction, approximately 90% of the fiber is contained in the parallel quoit or warp yarns 2.

The sleeve yarns 5, which consist completely of absorbable material, are generally about 130 denier. On transfer they are given a nominal 1.4 turn per inch (TPI) 'Z' or 'S' twist before further processing. This facilitates handling and minimizes fiber breakage.

The quoit (stuffer or warp) yarns can be 100% absorbable or they may contain a nonabsorbable component. They are much heavier than the sleeve, generally ranging from 2100 to 2700 denier. This necessitates two passes on a six position ply twister. A 130 denier yarn would normally be 5-plied 2.8 TPI 'S' or 'Z', then 4 ends of the 5-ply yarn would be twisted 1.4 TPI in the reverse direction. This would result in a final quoit yarn denier of 2600, mechanically balanced from the reverse twist operation (no tendency to twist or unravel).

Nonabsorbable components 6, if included, are blended into the quoit yarns during the 1st ply twisting operation. For instance, a J MAXON TM-/NOVAFIL® (American Cyanamid Co., N.J. 07470 U.S.A.) bicomponent yarn consisting of 18–22% nonabsorbable fiber would be made by running 1 yarn of 130 denier NOVAEIL® with 4 yarns of 130 denier MAXON TM in the 5-ply operation. The preparation and polymeric composition of MAXON TM is disclosed in U.S. Pat. Nos 4,423,660; 4,300,565 and 4,243,775; the preparation and polymeric composition of NOVAFIL® is disclosed in U.S. Pat. Nos. 4,314,561; 4,246,904; and 4,224,946. All of these patents are incorporated herein by reference. The exact proportion of NOVAFIL® is determined by the yarn deniers involved and the proportion of quoit yarns in the braid construction.

An important processing step for some absorbable yarns is post treatment (a vacuum annealing step which upgrades the implant tensile values). Generally speaking, for a construction that is to be 100% absorbable, the yarns are post treated after ply twisting: for an absorbable/nonabsorbable bicomponent construction, the absorbable yarns are post treated prior to ply twisting. There is another option and that is to post treat the final braid, providing it does not have a deleterious effect on a nonabsorbable component.

After ply twisting and post treatment, the yarns are ready for braiding. The best results to date are obtained with a construction that is made on a 13 carrier flat braider, which has 6 quoit gap feed. About 90% of the construction is composed of the heavy parallel quoit yarns held loosely together by the sleeve yarns at 12.3 picks (yarn cross over points) to the inch. After braiding, the ligament is ready for further processing. It is cut to length and sleeved on both ends with a ¼" aluminum or silver sleeve. A stainless steel overcap 3 with a small metal swivel pin 7 is then attached.

The end capped ligaments are now ultrasonically washed in xylol to remove any residual finishing oils (6 min residence in each of 4 baths). After the implants are air dried, appropriate needles 4 are attached to the metal pins to allow the implant to swivel in use. They are then packaged in preformed plastic trays with a lid and in open aluminum foil laminate envelopes. They are sterilized in an Ethylene Oxide cycle which includes an elevated temperature vacuum drying step. The foil laminate envelopes containing the dry ligaments are then heat-sealed in an aseptic glove box hood fed by dry air. Any interim storage needed between vacuum drying and heat sealing is carried out in an aseptic sealed box fed, again, by dry air.

Figure 4:
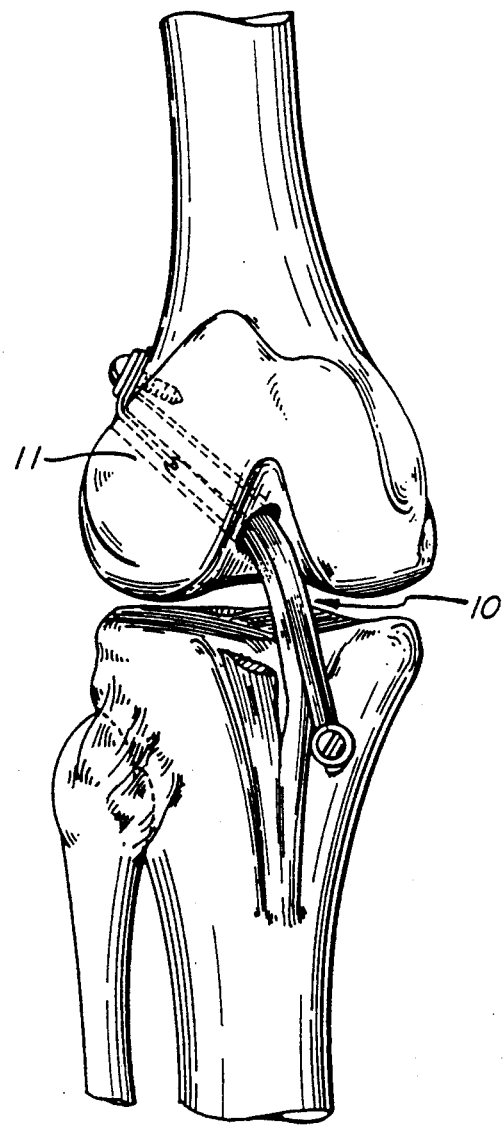
FIG. 4 is an anterior view of a knee showing the device as positioned for augmentation of the medial third of the patellar ligament in an Anterior Cruciate Ligament reconstruction.

Devices, as described above, may be surgically implanted to bridge a defect in a ligament, as a replacement for an excised damaged ligament (FIG. 3) or as an augmentation (FIG. 4) for autogenous tissue graft (or allograft) ligament reconstruction. In those surgical procedures requiring passage through and/or attachment to soft tissue 9, implants having the end-cap 3 and swivel needle(s) 4 at the end(s) would be used. For those applications in which the implant only needs to be passed through an open joint space 10 or through pre-drilled tunnels in bone 11, the swivel needles would not be required. Implants provided for such procedures may instead have either: (a) melt-fused ends to prevent fraying, or (b) ends stiffened by surrounding tubes 8 that are melt-fused or heat-shrunk onto the material of the device itself.

The invention can be described by the following examples.

EXAMPLE 7

This embodiment consisted of 100% MAXON™ in a flat braid construction. It differs from constructions described in previous examples in that it was airjet texturized prior to the initial twisting steps. The sleeve yarn consisted of 149d texturized MAXON™. This was made by overfeeding 2 yarns of 66 denier MAXON™ into the airjet chamber-one by 15% and the other by 8%. This material was then twisted to 1.4 TPI 'Z'. The quoit yarn started with 219 denier texturized MAXON™. This was made by overfeeding 1 ; end of 66d MAXON™ at 15% into the airjet along with 1 end of 130d MAXON™ at 8%. The 219 denier yarns were then 3-plied at 2.8 TPI 'S'. Four yarns of the 3-ply material were then reverse twisted at 1.4 TPI 'Z' to give a final denier of 2523.

This material was braided on a 13 carrier flat machine at 12.3 picks per inch. Its final denier measured 17.693 with 88.7% of the construction in the quoits.

The straight pull to break averaged 130 lbs (3.3 gms per denier) with an extension at break of 26.7%. As expected, its surface appearance resembled that made of yarns spun from a natural, staple fiber such as cotton or wool. Optically, the braid could be characterized as having a loose, single fil looped appearance. Subsequent processing of the braid is as described above under the heading 'Description of the Preferred Embodiment'.

EXAMPLE 8

This design is identical to Example 11 except that in the initial 3-plying of the quoit yarns one end of a 245 denier MAXON™/NOVAFIL® texturized bicomponent yarn was substituted for one of 219 denier texturized MAXON™ yarns. This MAXON™/NOVAFIL® bicomponent was made by overfeeding a 66d MAXON™ yarn at 55% and two 69d NOVAFIL® yarns at 11% into the airjet chamber. The denier of the 12 ply quoit yarn was measured to be 2667d.

This material was braided on a 13 carrier flat machine at a 12.3 pick. Its final denier was 18,467 of which 89.2% was quoit yarn and 19.1% was the nonabsorbable NOVAFIL® component.

The final non-sterile ligament had a breaking strength of 122 lbs (3.00 grams per denier) and an extension at break of 25.9%. Hydrolytic data indicates that this will make a viable product with a residual strength of 29.5 lbs.

Subsequent processing of the braid is as described above under the heading 'Description of the preferred Embodiment'.

EXAMPLE 9

This implant design is identical to Example 11 except that in the initial 3 plying of the quoit yarns one end of a 226 denier MAXON™/Heat Stretched Texturized DACRON® bicomponent yarn was substituted for one of the 219 denier MAXON™ yarns. This MAXON™/Heat Stretched DACRON® bicomponent was made by overfeeding a 66 denier MAXON™ yarn at 55% and a 127 denier heat stretched MACRON® yarn at 11% into the airjet chamber. The denier of the 12 ply quoit yarn measured 2613.

This material was braided on a 13 carrier flat machine at a 12.3 Pick. Its final non-sterile denier was 18.054, of which 89.0% was quoit yarn and 20.7% was the nonabsorbable heat stretched DACRON®

The final non-sterile ligament had a breaking strength of 97 lbs (2.43 grams per denier) and an extension at break of 21.7%. Hydrolytic data indicated it would remain unchanged in strength for 14 days and would have a residual strength of 34.7 lbs.

Subsequent processing of the braid is as described above under the heading 'Description of the preferred Embodiment '.

EXAMPLE 10

This construction consists of 100% MAXON TM in a flat braid construction. It differs from previous constructions in that it is braided on a 21 carrier machine.

The sleeve yarn consists of 66 denier MAXON TM yarn twisted to 1.4 TPI 'Z'. The 130 denier quoit yarns are first 2-plied at 2.8 TPI 'S'—then 5 yarns of this 2-ply construction are reverse twisted at 1.4 TPI 'Z'. The final denier of the 10 ply quoit yarn is 1300.

The above yarns are then braided on a 21 carrier machine with 10 quoit yarns set at a 12 picks/inch. The final construction measures 16,986 denier, of which 91.8% is quoit yarn.

Samples are expected to have a non-sterile breaking strength of 124 lbs (equivalent to 3.31 grams per denier) with an extension at break of 35.2%.

EXAMPLE 11

This construction consists of 100% MAXON TM in a flat braid construction. It differs from previous constructions in that it is braided on a 15 carrier machine.

The sleeve yarn consists of 98 denier MAXON TM twisted to 1.4 TpI Z. The 130 denier quoit yarns are 5-plied at the same level of twist to give a total denier of 650. All yarns are post treated after plying.

The above yarns are braided on a 45 carrier machine. Only 15 out of 45 available carriers are used for the sleeve yarns. All of the available 22 quoit positions are used. The braider is set for a 4.1 pick. The final construction measures 15,770 denier, of which 90.7% is parallel quoit yarn.

Straight pull tensile strength is expected to average approximately 68 lbs (4.83 grams/denier) with a 37.2% elongation at break.

EXAMPLE 12

This implant design is similar to Example 15 except that 1 yarn of heat stretched DACRON TM is substituted in ply twisting the quoit yarns. Also, all MAXON TM yarns are post treated prior to twisting.

The final braid denier is 15,700, of which 90.7% is parallel quoit yarn. Approximately 18.1% of the total construction is the nonabsorbable DACRON ® component.

Straight pull tensile strength is expected to be approximately 127 lbs (3.67 grams/denier) with a breaking elongation of 29.3%. Hydrolytic data from similar constructions indicate that this design would make a viable product with a residual strength of 29 lbs due to the nonabsorbale component.

EXAMPLE 13

This design consists of 100% MAXON TM in a flat braid construction. Although braided on a 45 carrier machine, it differs from Sample 15 in that it is 3.3 times heavier.

The sleeve yarns consist of 130 denier MAXON TM twisted to 1.4 TPI 'Z'. The 130 denier quoit yarns were first 4-plied to 2.8 TPI 'Z', then four 4-ply yarns are reverse plied to 1.4 TPI 'S' to give a final quoit yarn denier of 2080. All yarns are post treated after twisting.

The above yarns are then braided on a 45 carrier machine using all available carriers for the sleeve and all of the available 22 quoit yarn positions. The braider is set for a 12.3 pick. The final construction measures 51,610 denier, of which 88.7% is parallel quoit yarn.

Straight pull tensile strength is expected to average 525 lbs (4.61 grams/denier) with a breaking elongation of 31.6%.

Although the following example, and variations thereof, may be suitable for some soft tissue orthopedic (i.e. tendon) repair/reconstruction applications, it has been found to be inappropriate as a ligament implant and therefore not part of this invention. It is disclosed for its comparative value to examples 7 to 13, and as a contribution to the state of the art.

Comparative Example A

This implant design was 100% DEXON ® (PGA) in a flat braid configuration and again consisted of heavy denier quoit or warp yarns held together by light denier sleeve yarns. However, all the yarns were post treated: then air jet texturized prior to twisting and braiding.

a. The quoit (warp) yarn consisted of a 6 ply construction using 357 denier texturized DEXON ® yarn to give a total 2142 denier yarn. This 357 denier yarn was made by entangling 3 ends of 110 denier DEXON ® yarn - 2 yarns with a 24% overfeed and one with a 6% overfeed.

b. The sleeve yarn was made similarly except it was a 152 denier, texturized DEXON ® yarn. This was made by entangling 2 yarns of 62 denier DEXON ®—one yarn with a 24% overfeed and the other with an 11% overfeed.

c. The braid was made on a thirteen carrier braider, each carrier containing the 152 denier yarn described in section b above. These sleeve yarns were braided about the 2142 denier warp yarns fed through all six available quoit positions. The total pick count was estimated at 12.3 per inch.

The total braid denier was 14,800. Tensile strength measured 152 lbs. with a 23.2% elongation-to-break.

Connective tissue devices of this construction were evaluated in-vivo. Upon sacrifice at 2 months, these implants were found to have better tissue ingrowth/organization than non-texturized PGA devices. However, the results achieved with implants made using the longer lasting GTMC yarns were consistently, significantly improved over those obtained with the devices of this comparative example.

We claim:

1. A method of texturizing a plurality of fibers or yarns comprising:
   (1) deforming the plurality of fibers or yarns by twisting in one direction;
   (2) setting the deformation of said plurality of fibers or yarns from step (1) by twisting in the opposite direction without removing the deformation;
      (a) heating them to their glass transition temperature under a vacuum of up to about 5 torr; and
      (b) cooling the fibers or yarns to ambient temperature; and
   (3) mechanically removing the twist inserted in the fibers or yarns from step (1).

2. A method of claim 1 wherein the vacuum in the heating step is at or less than about 1 torr.

3. A method of claim 1 wherein the relative humidity of the atmosphere in the heating step is up to about 25%.

4. A method of claim 3 wherein said relative humidity of said atmosphere is up to about 15%.

5. A method of claim 4 wherein said relative humidity is less than about 5%.

6. A method of texturizing a plurality of fibers or yarns comprising:
   (1) deforming the plurality of fibers or yarns by twisting in one direction;
   (2) setting the deformation of said plurality of fibers or yarns from step (1) by
      (a) heating them to a temperature of from about 100° to 190° C. under a vacuum of up to about 5 torr;
      (b) cooling the fibers or yarns to ambient temperature; and
   (3) mechanically removing the twist inserted in the fibers or yarns fronm step (1) by twisting in the opposite direction without removing the deformation; fibers or yarns from step (1) by twisting in the opposite direction without removing the deformation;

7. A method of claim 27 wherein the temperature in the heating step is about 120° to 140° C.

8. A method of claim 7 wherein the vacuum in the heating step is at or less than about 1 torr.

9. A method of claim 6 wherein the relative humidity of the atmosphere in the heating step is from about 5 to 25%.

10. A method of claim 9 wherein said relative humidity of said atmosphere is from about 5 to 15%.

11. A method of claim 6 wherein the relative humidity of the atmosphere in the heating step is less than about 5%.

12. A method of claim 1 or claim 2 comprising after the removing step:
   (4) resetting the plurality of fibers or yarns from step (3) by
      (a) reheating and then
      (b) recooling them as described in steps (2)(a) and (b), respectively.

* * * * *

UNITED STATES PATENT OFFICE
CERTIFICATE OF CORRECTION

Patent No. 4,987,665  Dated  January 29, 1991

Inventor(s) Barry Lee Dumican, and Barbara Andrews

It is certified that error appears in the above-identified patent and that said Letters Patent is hereby corrected as shown below:

Claim 1, column 16, lines 52 to 53, delete "twisting in the opposite direction without removing the deformation;"

Column 16, line 59, after "step (1)" add -- by twisting in the opposite direction without removing the deformation --

Claim 6, column 17, line 15, delete "fronm" and substitute -- from --

Column 17 delete lines 17 to 19 (i.e., the last three lines of claim 6) and substitute -- tion. --

Signed and Sealed this

Ninth Day of June, 1992

Attest:

DOUGLAS B. COMER

Attesting Officer     Acting Commissioner of Patents and Trademarks